United States Patent
Naudet et al.

(10) Patent No.: US 6,629,463 B2
(45) Date of Patent: Oct. 7, 2003

(54) ACOUSTIC INSPECTION OF ONE-PIECE BLADED WHEELS

(75) Inventors: Jacky Naudet, Bondoufle (FR); Jean-Luc Mary, Pamfou (FR); André Collot, Mennecy (FR); Marc Berthillier, Yerres (FR)

(73) Assignee: Snecma Moteurs, Paris (FR)

( * ) Notice: Subject to any disclaimer, the term of this patent is extended or adjusted under 35 U.S.C. 154(b) by 0 days.

(21) Appl. No.: 09/971,614

(22) Filed: Oct. 9, 2001

(65) Prior Publication Data

US 2002/0059831 A1 May 23, 2002

(30) Foreign Application Priority Data

Oct. 10, 2000 (FR) .............................. 00 12926

(51) Int. Cl.$^7$ .............................................. G01N 29/04
(52) U.S. Cl. .................... 73/579; 73/12.01; 73/597; 73/598; 73/602
(58) Field of Search ................... 73/579, 584, 593, 73/598, 600, 602, 659, 660, 11.01, 587, 12.01; 702/56, 35, 39, 76

(56) References Cited

U.S. PATENT DOCUMENTS

| | | | |
|---|---|---|---|
| 4,052,889 A | 10/1977 | Mucciardi et al. | 73/602 |
| 4,213,183 A | 7/1980 | Barron et al. | 702/39 |
| 4,422,333 A * | 12/1983 | Leon | 73/660 |
| 4,956,999 A * | 9/1990 | Bohannan et al. | 73/587 |
| 4,980,844 A * | 12/1990 | Demjanenko et al. | 702/56 |
| 4,996,880 A * | 3/1991 | Leon et al. | 73/660 |
| 4,998,005 A | 3/1991 | Rathi et al. | 219/121.83 |
| 5,048,320 A * | 9/1991 | Mitsuhashi et al. | 73/12.09 |
| 5,152,172 A * | 10/1992 | Leon et al. | 73/579 |
| 5,253,531 A * | 10/1993 | Walker et al. | 73/650 |
| 5,258,923 A * | 11/1993 | Imam et al. | 702/36 |
| 5,365,787 A * | 11/1994 | Hernandez et al. | 73/660 |
| 5,445,027 A * | 8/1995 | Zorner | 73/593 |
| 5,471,880 A * | 12/1995 | Lang et al. | 73/660 |
| 5,663,894 A * | 9/1997 | Seth et al. | 702/56 |
| 5,686,652 A * | 11/1997 | Pfund | 73/12.04 |
| 5,728,949 A * | 3/1998 | McMillan | 73/861.77 |
| 5,895,857 A * | 4/1999 | Robinson et al. | 73/660 |
| 5,907,098 A * | 5/1999 | Tsuboi et al. | 73/579 |
| 6,094,989 A * | 8/2000 | Twerdochib | 73/659 |
| 6,208,944 B1 * | 3/2001 | Franke et al. | 702/56 |
| 6,321,602 B1 * | 11/2001 | Ben-Romdhane | 73/660 |
| 6,371,218 B1 * | 4/2002 | Amano et al. | 173/183 |
| 6,381,547 B1 * | 4/2002 | Heirtzler et al. | 702/39 |
| 6,382,027 B1 * | 5/2002 | Uhlig | 73/579 |
| 6,456,927 B1 * | 9/2002 | Frankowski et al. | 701/111 |
| 6,487,909 B2 * | 12/2002 | Harrold et al. | 73/593 |

* cited by examiner

*Primary Examiner*—Helen Kwok
*Assistant Examiner*—Jacques Saint-Surin
(74) *Attorney, Agent, or Firm*—Oblon, Spivak, McClelland, Maier & Neustadt, P.C.

(57) ABSTRACT

These objects are achieved by a method of acoustically inspecting a one-piece bladed wheel in which the wheel is driven in rotation; each blade of the wheel is subjected to mechanical excitation; its acoustic response is picked up and a corresponding electrical signal is generated; its frequency response is determined by computing a FFT; the electrical signal and the associated frequency response are stored; the characteristic frequencies of each blade of the wheel are identified; and a wheel is rejected or accepted depending on whether or not the frequency distribution obtained in this way matches a predetermined set of forbidden frequency distributions. Advantageously, an additional step is provided in which the defects of a blade are determined by comparing its frequency response with predetermined frequency responses that are characteristic of various types of defect.

7 Claims, 2 Drawing Sheets

ACOUSTIC INSPECTION OF ONE-PIECE BLADED WHEELS

FIELD OF THE INVENTION

The present invention relates to the field of inspecting the machining of mechanical parts, and more particularly it relates to frequency inspection of one-piece bladed wheels by vibro-acoustic signature.

PRIOR ART

Until recently, the rotary portion or "rotor" of the compressor in a turbojet or a turbo-thruster (referred to below as a "turbomachine"), has been built up by assembling together a plurality of wheels in the form of disks or rings, with each wheel having blades, also known as "vanes", individually attached thereto. One consequence of individually mounting blades in that way is to cause vibratory phenomena to be damped, thereby making it impossible, in practice, for resonance to destroy a wheel on which blades are mounted.

Nowadays, compressor wheels, and also industrial fan wheels, are being made more and more frequently as single pieces, with the blades being integral with the wheel disk or support ring. That type of structure serves to minimize the size and the weight of the wheel and thus also of the compressor as a whole, which is beneficial for the overall mass of the turbomachine that incorporates it.

Unfortunately, modern means for automatic machining enable very great precision and very great repeatability to be achieved in the manufacture of blades, and an unexpected consequence of an almost perfect shape being made is to provoke very large resonant vibratory phenomena which can, under extreme circumstances, lead to the wheel being completely destroyed.

OBJECT AND DEFINITION OF THE INVENTION

An object of the present invention is to provide a method- and a corresponding apparatus for acoustic inspection of one-piece bladed wheels that enable this risk of resonance to be identified, in order to avoid potential destruction of the wheel. Another object of the invention is to propose an inspection method which is particularly fast and which can be implemented in real time. Another object of the invention is to propose an inspection method which can form an integral portion of the machining process. Yet another object of the invention is to propose a method which also makes it possible to inspect the quality of the machining. A further object of the invention is to propose a method which can also determine the types of defect that affect any blades found to be defective.

These objects are achieved by a method of acoustically inspecting a one-piece bladed wheel in which the wheel is driven in rotation; each blade of the wheel is subjected to mechanical excitation; its acoustic response is picked up and a corresponding electrical signal is generated; its frequency response is determined by computing a fast Fourier transform (FFT); the electrical signal and the associated frequency response are stored; the characteristic frequencies of each blade of the wheel are identified; and a wheel is rejected or accepted depending on whether or not the frequency distribution obtained in this way matches a predetermined set of forbidden frequency distributions.

With this particular method, it is possible for a wheel that is not compliant to be identified very quickly and without error. Furthermore, the method can be integrated without difficulty in a conventional machining process.

Preferably, the method also includes an additional step of determining the defects of a blade by comparing its frequency response with predetermined frequency responses that are characteristic of various types of defect.

The invention also provides apparatus implementing the above method. Advantageously, the mechanical excitation means of the apparatus comprise means for excitation by percussion or by releasing a hammer, and the acoustic receiver means comprise a microphone.

BRIEF DESCRIPTION OF THE DRAWINGS

The characteristics and advantages of the invention appear more fully from the following description given by way of non-limiting indication, and with reference to the accompanying drawings, in which.

DETAILED DESCRIPTION OF A PREFERRED EMBODIMENT

Figure 1:
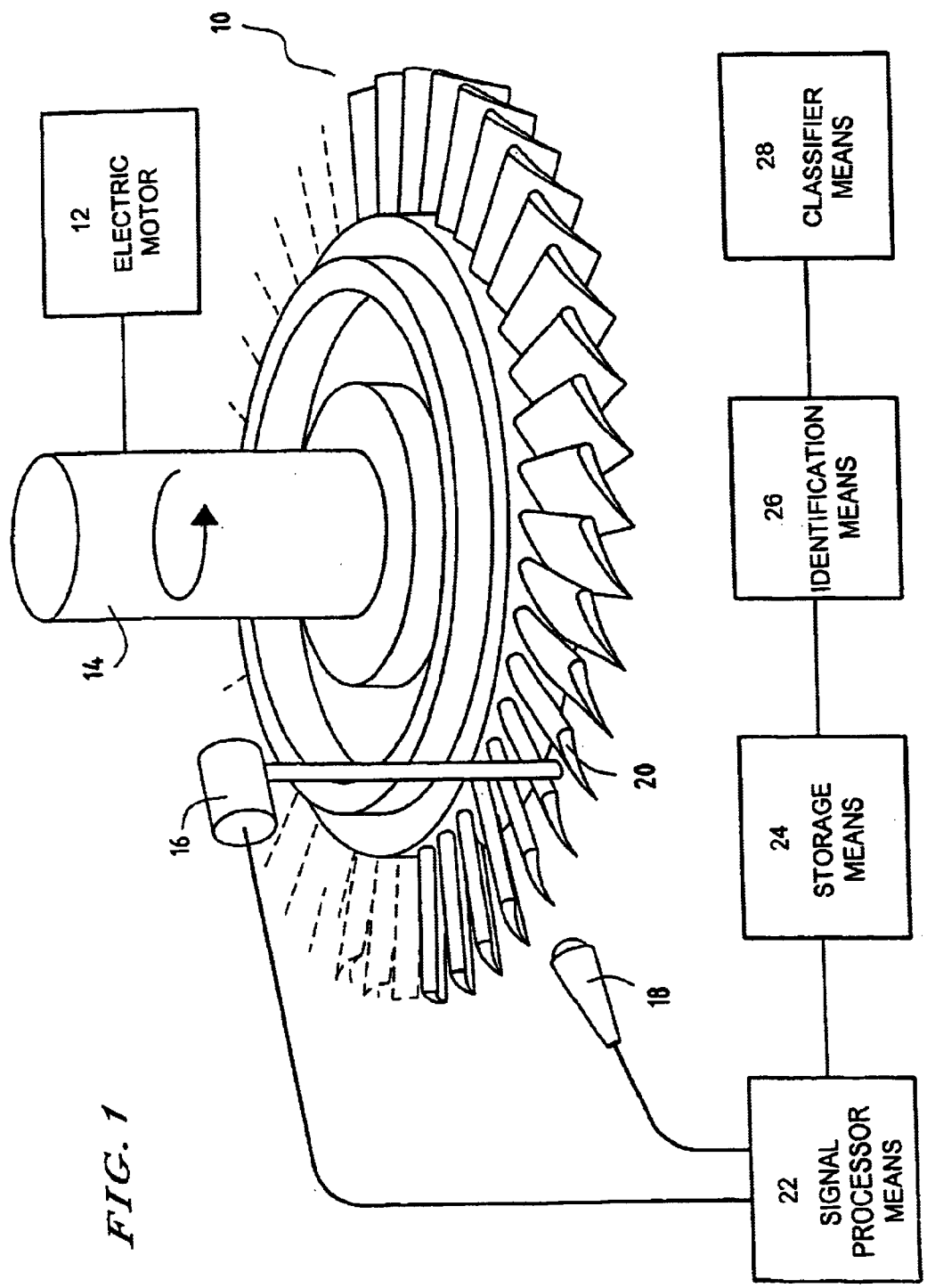
FIG. 1 is an overall diagrammatic view showing the apparatus of the invention for acoustically inspecting one-piece bladed wheels.

The apparatus of the invention for acoustically inspecting one-piece bladed wheels is shown very diagrammatically in FIG. 1. It comprises means for rotating a wheel 10, which means are constituted, for example, by an electric motor 12 driving a hub 14 on which the wheel for inspection is placed (an indexing system, not shown, is also provided in order to identify each of the blades of the wheel); mechanical excitation means 16 are placed above a blade 20 of the wheel, by way of example these means can be constituted by a percussion device or by releasing a hammer (e.g. a metal strip or finger); acoustic receiver means 18, e.g. constituted by a microphone, are placed in the vicinity of the excited blade; and processor means 22–28 are connected to control the mechanical excitation means 16 and also to process the acoustic signals picked up from the terminals of the acoustic receiver means 18. Conventionally, for each blade of the wheel, processing of the acoustic signals is synchronized on the corresponding excitation signals.

The processor means comprise means 22 for transforming the picked-up acoustic signals into electrical signals. The transformation of the acoustic signals is conventionally associated with filtering over a determined frequency band compatible with the wheel under inspection. The signals are then subjected to fast Fourier transform (FFT) analysis in order to determine the frequency response of the corresponding blade. The analyzed electrical signals (after sampling) and the various samples of the resulting frequency response are stored in storage means 24, e.g. a digital memory, for each blade of the wheel under inspection. It will be observed that determining the frequency response of each blade and storing it in the storage means need not be performed stepwise for each blade, but can be performed overall after acoustic signals have been picked up for all of the blades of the wheel under inspection.

Figure 2:
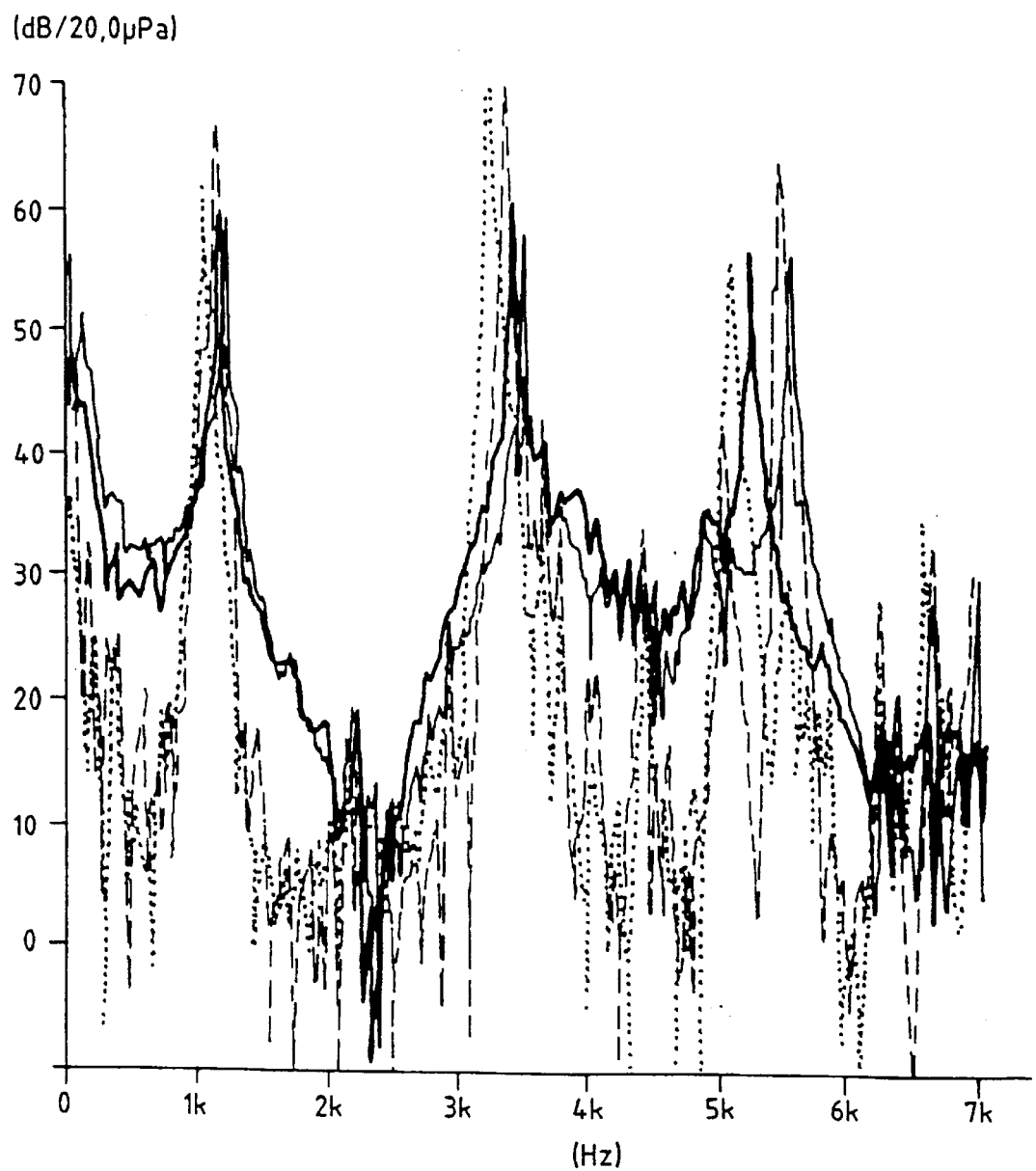
FIG. 2 is a graph showing an example of frequency response curves obtained using the apparatus of FIG. 1.

FIG. 2 shows an example of the frequency responses obtained for four successive wheels of a one-piece bladed compressor wheel for a turbomachine, with these frequency responses constituting a kind of acoustic signature for the blades. In the example shown, it can be seen that each blade presents three particular frequencies F1, F2, and F3 that are characteristic of the shape of the blade being inspected. Measurement was performed over a frequency range of 0 to 7000 hertz (Hz) with frequency resolution of 8 Hz.

Processing performed on the frequency responses of each of the blades of the wheel under inspection by identification means 26 then enable the characteristic frequencies of each blade to be determined from the various frequencies supplied by the preceding frequency responses, giving rise to a table as follows:

| Blade number | Frequency F1 | Frequency F2 | Frequency F3 |
|---|---|---|---|
| 1 | $F1^1$ | $F2^2$ | $F3^1$ |
| 2 | $F1^2$ | $F2^2$ | $F3^2$ |
| ... | | | |
| i | $F1^i$ | $F2^i$ | $F3^i$ |
| ... | | | |
| n | $F1^n$ | $F2^n$ | $F3^n$ |

This table shows up clearly how the characteristic frequencies of the blades on a given wheel are dispersed. Thereafter, a wheel is rejected or accepted quite simply by classifier means 28 comparing the distribution of these characteristic frequencies in the resulting table with a predetermined set of forbidden frequency distributions, i.e. distributions which correspond to configurations that are unacceptable in terms of vibration, as determined during design of the wheel. If the resulting distribution matches a forbidden distribution, then the wheel under inspection is rejected.

The method of the invention for acoustically inspecting a one-piece bladed wheel can thus be summarized by the following steps:

a) driving the wheel in rotation;

b) subjecting a first blade to mechanical excitation;

c) picking up an acoustic response and generating a corresponding electrical signal;

d) performing an FFT computation to determine the frequency response of said first blade of the wheel;

e) storing the electrical signal and the associated frequency response;

f) repeating steps b) to e) for each blade of the wheel;

g) identifying characteristic frequencies of each blade of the wheel from the stored frequency responses; and h) rejecting or accepting a wheel depending on whether the resulting frequency distribution matches a predetermined set of forbidden frequency distributions.

This method is particularly efficient and very quick (complete analysis of a blade of the wheel can be performed in less than 2 seconds), and it makes it possible, practically without error, to decide on whether it is worthwhile to continue the manufacturing process. Manufacturing a one-piece bladed wheel generally comprises three successive operations: milling; polishing; and shot blasting. So by performing inspection at the end of the milling stage (directly on the machine before removing the wheel or else on a neighboring workstation), it is possible to avoid performing the two following stages if inspection reveals that a wheel is not compliant. This also makes it possible to avoid continuing the machining process on the following wheels having the same defects or waiting, as is the case at present, for subsequent geometrical inspection. It should also be observed that the speed of the inspection makes it possible to perform inspection in time that is "free" or "non-critical" relative to the operation of machining the next wheel. Under such circumstances, the rotary drive means can be constituted directly by the means used in the apparatus performing the machining.

In addition, various tests performed by the inventors have shown that the various departures of the frequency spectrum of a particular blade from that of an ideal reference blade are the result of defects in the shape or the structure of the blade. Thus, a geometrical defect that is not visible to the eye (e.g. extra thickness of only 10 microns) shows up in a frequency spectrum that presents modes which are offset relative to those of the ideal blade. This makes it possible to categorize certain classes of typical defects (truncated blade, excess thickness at blade root, local deformation, cracking, etc.) presenting particular frequency responses (or frequency spectra).

Thus, the method of the invention can be used not only to set aside without error any wheel that is likely to present dangerous resonance characteristics, but it also makes it possible, by comparing the frequency response of such rejected wheels with predetermined frequency responses characteristic of various types of defect, to determine the kinds of significant defects to which the wheels are subject and possibly to take steps to remedy them (for example extra thickness can be eliminated by new machining performed locally), thereby giving rise to a part that is compliant.

What is claimed is:

1. A method of acoustically inspecting a one-piece bladed wheel, the method comprising the following steps:

a) driving the wheel in rotation;

b) subjecting a first blade to mechanical excitation;

c) picking up an acoustic response and generating a corresponding electrical signal;

d) performing an FFT computation to determine the frequency response of said first blade of the wheel;

e) storing the electrical signal and the associated frequency response;

f) repeating steps b) to e) for each blade of the wheel;

g) identifying characteristic frequencies of each blade of the wheel from the stored frequency responses; and h) rejecting or accepting a wheel depending on whether the resulting frequency distribution matches a predetermined set of forbidden frequency distributions.

2. An acoustic inspection method according to claim 1, wherein said steps for determining the frequency response and storing it are performed after all of the electrical signals have been picked up from the wheel.

3. An acoustic inspection method according to claim 1, wherein said mechanical excitation consists in excitation by impact or by releasing a hammer.

4. An acoustic inspection method according to claim 1, further comprising a step of determining defects in a blade by comparing its frequency response with predetermined frequency responses characteristic of various types of defect.

5. Apparatus for acoustically inspecting a one-piece bladed wheel, the apparatus comprising:

a) drive means for rotating said wheel;

b) mechanical excitation means for subjecting each of the blades of the wheel to mechanical excitation;

c) acoustic receiver means for picking up an acoustic response and for generating a corresponding electrical signal;

d) computation means for computing the frequency responses of each blade of the wheel by means of an FFT;

e) storage means for storing the electrical signals and the associated frequency responses;

f) identification means for identifying characteristic frequencies of each blade of the wheel on the basis of their stored frequency responses; and g) classifier means for rejecting or accepting a wheel depending on whether or not the resulting frequency distribution matches a predetermined set of forbidden frequency distributions.

6. Acoustic inspection apparatus according to claim 5, wherein said mechanical excitation means comprise means for excitation by percussion or by releasing a hammer.

7. Acoustic inspection apparatus according to claim 5, wherein said acoustic receiver means comprise a microphone.

* * * * *